(12) United States Patent
Hofmeier et al.

(10) Patent No.: US 6,673,086 B1
(45) Date of Patent: Jan. 6, 2004

(54) APPARATUS FOR THE MICRO-DISSECTION OF TISSUE

(75) Inventors: Gerhard Hofmeier, Hamburg (DE); Hartmut Schmidt-Rabenau, Hamburg (DE); Axel Niendorf, Hamburg (DE)

(73) Assignee: Eppendorf AG, Hamburg (DE)

(*) Notice: Subject to any disclaimer, the term of this patent is extended or adjusted under 35 U.S.C. 154(b) by 0 days.

(21) Appl. No.: 09/613,088

(22) Filed: Jul. 10, 2000

(30) Foreign Application Priority Data

Jul. 9, 1999 (DE) .......................... 199 32 032

(51) Int. Cl.[7] ............................................. A61B 17/32
(52) U.S. Cl. ..................................................... 606/169
(58) Field of Search .................... 606/169, 167, 606/170, 171, 177, 178, 182, 187, 166

(56) References Cited

U.S. PATENT DOCUMENTS

| | | | |
|---|---|---|---|
| 4,154,228 A | * | 5/1979 | Feldstein et al. ............ 606/169 |
| 5,288,292 A | * | 2/1994 | Giraud et al. ................ 606/166 |
| 5,735,868 A | * | 4/1998 | Lee .............................. 606/169 |

* cited by examiner

*Primary Examiner*—Kevin T. Truong
(74) *Attorney, Agent, or Firm*—Sidley Austin Brown & Wood, LLP

(57) ABSTRACT

An apparatus for the micro-dissection of tissue with a fine needle, which is arranged on holder movable in space along three axes and the tip of which can be moved with the holder relative to the tissue, which is to be severed, wherein the needle is coupled with an oscillating drive mechanism, which causes the needle to oscillate in the longitudinal and/or transverse direction at a predetermined amplitude and frequency.

8 Claims, 1 Drawing Sheet

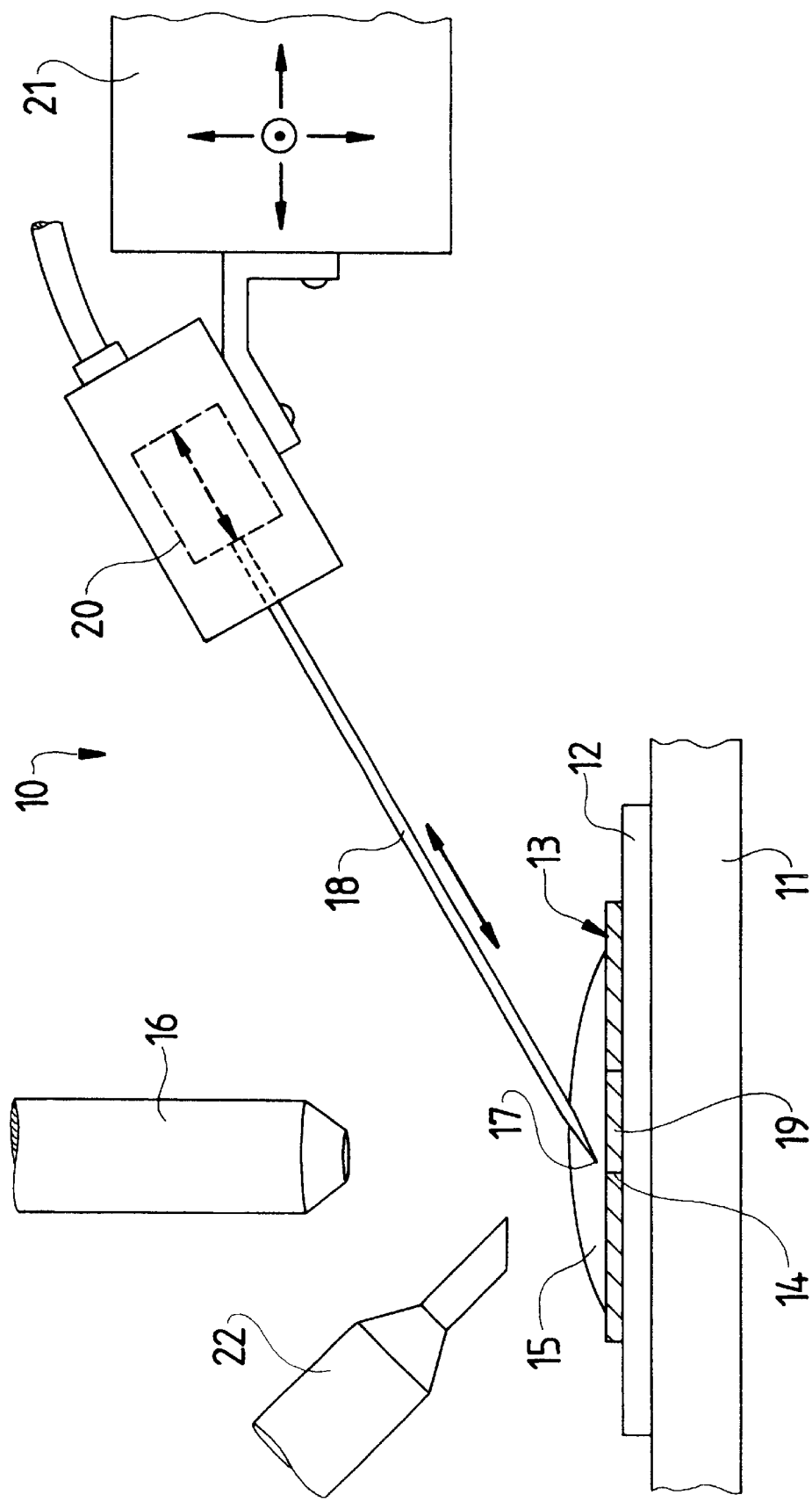

APPARATUS FOR THE MICRO-DISSECTION OF TISSUE

BACKGROUND OF THE INVENTION

1. Field of Invention

The invention relates to a device for the micro-dissection of tissue with a fine needle, which is supported in a holder movable in space along three axes.

2. Description of the Prior Art

Generic devices are used, for example, in conjunction with the molecular-biological diagnosis of tumors, for which the DNA or RNA of cells is analyzed in sections of tumor tissue. The presence, for example, of certain DNA sequences permits conclusions to be drawn concerning the nature of the tumor and, insofar as statistical data are already available, concerning the course of the disease.

However, sections of tumor tissue do not contain tumor cells exclusively. As a rule, suspicious (that is, tumorous) cells are embedded in otherwise healthy cell tissue in such sections. If the whole of the section is investigated by molecular biological techniques, the danger exists that the DNA of the tumorous cells diminishes quantitatively relative to the DNA of the other cells to such an extent, that a detection of DNA sequences of certain tumor cells is no longer possible, at least not with a sufficient reliability.

There has therefore been a change in procedure in the direction of isolating tumorous tissue regions or cells, which can be identified under the microscope, from sections of such tumor tissues by micro-dissection, and by working up only these regions.

At the present time, different techniques are known for the micro-dissection of tissue. One possibility consists, for example, in severing the questionable region of tissue from the remaining tissue of the section by UV laser radiation and removing it then, for example, by aspiration, for further processing. A different known possibility consists in depositing a special film on the section and of "gluing" the film with infrared radiation to the surface of the tissue region. After gluing, the tissue region adheres so firmly to the film, so that it can be removed together with it from the tissue section. Both methods, however, are relatively expensive.

In the case of a different generic device, the tissue of interest is scratched with the optimally ground end of a steel cannula, which is moved with a conventional manipulator, out of the section, and the severed region of the tissue is removed for further processing with an aspiration or adhesion cannula. It is also known that, instead of a steel cannula, a finely drawn out glass cannula can be used, the tip of which, optionally, is broken or sharpened in a different way. Working with the described "scratching" cannula is very laborious. Moreover, the danger exists that the section will tear in an uncontrolled manner.

Accordingly, an object of the invention is to provide an apparatus for micro-dissection, which makes a more convenient and more reliable severing of tissue possible and, moreover, can be realized relatively inexpensively.

SUMMARY OF THE INVENTION

This and other objects of the present invention, which will become apparent hereinafter, are achieved by coupling the needle to an oscillating drive mechanism for oscillating the needle in longitudinal and/or transverse directions with a predetermined amplitude and frequency.

For micro-dissections, the inventive apparatus, as is known from the state of the art, uses a fine needle, which is disposed in a holder of a conventional manipulator, which can be moved in space along three axes.

In its simplest embodiment, a manipulator, which can be used in the inventive apparatus, only has a movable holder. Usually, but not necessarily, the movable holder is connected with a microscope in such a manner that, with the free end of an instrument, held in the holder, it is possible to work under optical control on an object, disposed on the microscope stage.

According to the invention, as discussed above, the needle, which is used for the micro-dissection, is coupled with an oscillating drive mechanism, which can cause the needle to oscillate in longitudinal and/or transverse direction with a selectable frequency and amplitude.

In operation, the free end of the oscillating needle is purposefully brought into contact with selected regions of the tissue, the latter being severed and broken up.

There exist different methods of operating the needle of the inventive device, depending on the direction of oscillation of the needle.

According to the first method, the needle is oscillated longitudinally by the oscillating drive mechanism, then guided for dissection along the edge of the region of tissue of interest, severing the latter as a whole from the section of tissue. When this method of the invention is used, the frequency of the needle is selected so that, as far as possible, only longitudinal oscillations occur and transverse resonance oscillations are avoided.

According to the second method, of the invention, the needle and the oscillating drive mechanism are coupled so that the needle oscillates transversely. In this case, the tissue region is not cut free along a line. Rather, the region of tissue of interest is scratched out piece by piece with the end of the transversely oscillating needle. With this method, especially several small regions of tissue can be detached from a section of tissue more quickly than they can with the first method.

Both methods can be realized without major problems by appropriately constructing the inventive apparatus.

In this connection, however, the first and second methods do not necessarily presuppose a differently directed coupling of oscillating drive mechanism and needle. In the case of a device, in which the needle is caused to oscillate longitudinally, it is also conceivable to select the frequency so that, aside from a basic longitudinal oscillation (optionally with a very small amptitude), transverse resonance oscillations occur in the tip region of the needle, with which a procedure in the above-described second manner is then also possible.

With this first method, the tissue, severed in one piece, can be removed from the section by aspiration or by an adhesion cannula. With the second method, preferably the liquid over the tissue section, together with the detached tissue fragments, are aspirated from the section and collected.

For both methods, if the oscillation frequency and amplitude are adjusted appropriately, the needle can easily penetrate with its tip into the usual tissue and break it up or divide it.

Since tissue sections usually are very thin, an amplitude in the micrometer range is, in most cases, sufficient when the first method is used. If the device is operated according to the second method, the amplitude of the transverse oscillations of the needle should be selected so that it is clearly less than the diameter of the tissue region, which is to be severed, so that the sample is prepared as cleanly as possible.

In order to avoid adverse effect on the operator's hearing, the frequency should preferably be selected outside of the audible range, that is, in the ultrasonic region. Basically, however, a frequency is sufficient, which ensures that the tip region of the needle oscillates so quickly in the tissue, that the directly adjoining tissue regions do not produce any mechanical stresses that interfere with the dissection. In other words, the frequency should be adjusted so that the tissue regions, which come into contact with the moving needle only laterally, are moved only insignificantly if at all by the latter. In this way, it is ensured that only the desired region of tissue actually is broken up or severed by the tip of the needle and that a tearing off or detachment of adjoining regions is avoided.

Preferably, the needle is an etched steel needle. However, the needle may also be formed of glass, hard metal or tungsten. It is also possible to grind the end of the needle. However, it has turned out that the distal contour of the needle is relatively unimportant for practicing the invention. The concept of needle should, therefore, not be defined too narrowly within the scope of the invention. It should include essentially any fine extended instrument with an end region, the dimensions and contour of which permit penetration into the tissue that is to be investigated. In particular, in the case of the above-mentioned second method, the needle need not necessarily run out into a point, but may also have a transverse, concluding edge, which enables the tissue piece to be scraped out more easily.

For producing oscillations, a conventional oscillating drive mechanism can be used. For example, the drive mechanism can be an electro-dynamic one. Preferably, however, a piezo element is used for producing the oscillations.

The oscillating drive mechanism is preferably arranged on the holder, which is movable in space along the three axes. The needle can then be coupled with the drive mechanism depending on the required direction of oscillation.

A further development of the invention relates to the optimum positioning of the needle during the dissection. It is obvious that with these methods, the tip of the needle must penetrate as far as possible into the tissue. However, contact between the tip and the surface of the microscope slide, which carries the section and usually consists of glass, should be avoided. In this connection, one embodiment provides a sensor in the inventive device, which is able to determine the optimum position of the needle. This sensor may conceivably be, for example, an oscillations sensor disposed in the oscillating drive mechanism. When such a sensor is used, the needle initially would be positioned so that its tip touches the microscope slide. It is then moved upward until the oscillations sensor indicates free oscillations; this would then correspond to an optimum position. Another possibility would be, for example, to arrange an acoustic sensor in the region of support holding the tissue section. This sensor records contact between the microscope slide and the tip of the needle and then adjusts the position appropriately.

As stated above, the inventive apparatus usually works with a manipulator, which at the very least has a needle holder movable in space along the three axes. It is, however, conceivable to couple this holder with different cell-biological instruments. The invention is, therefore, not directed only to the above-described device in its totality. Rather, the invention is also intended to cover a unit of a needle and an oscillating drive mechanism, which can be used optionally as an exchangeable accessory for conventional manipulators used in cell biology.

BRIEF DESCRIPTION OF THE DRAWINGS

The objects and features of the present invention will become more apparent and the invention itself will be best understood from the following detailed description of the present invention when read with reference to the accompanying drawings, wherein:

Single FIGURE shows a schematic view of the inventive apparatus.

DETAILED DESCRIPTION OF THE PREFERRED EMBODIMENT

The FIGURE shows an inventive apparatus 10 for micro-dissection. The apparatus comprises a support 11 for a microscope slide 12, on which a tissue section 13 is disposed. A region 19 is to be severed along a line 14 from the tissue section 13 by micro-dissection. The section 13 is partially covered with a liquid 15 particularly in the region bounded by the line 14. Preferably, a liquid is selected which, on one hand, has the necessary optical transparency and, on the other, contains, for example, substances which are deliberately selected with respect to the subsequent processing. It is, for example, conceivable to have RNase-inhibiting substances, such as chaotropic salts or the like in the liquid. The liquid may also, of course, be distilled water or a sodium chloride solution or also an organic solvent, to name but a few further possible examples.

Above the support 11, a microscope is disposed, of which only the objective 16 is shown in this FIGURE.

Pursuant to the invention, a needle 18, which has a fine point 17, is provided for the micro-dissection of the tissue region 19 bounded by the line 14. The needle 18 is coupled with an oscillating drive mechanism 20, which is indicated only diagrammatically and causes the needle 18 to oscillate longitudinally in the direction of the arrow. The oscillating drive mechanism 20, in turn, is disposed at a holder 21, which can move in space along the three axes.

By the movable holder 21, the point 17 of the needle is positioned in such a manner in or at the edge 14 of the region of tissue 19 that is to be detached, that severing of the tissue occurs upon oscillation. The tip 17 of the needle must then merely be guided with the seat 21 along the edge 14 of the tissue region 19, as a result of which the latter is severed from the remaining tissue.

The severed tissue region 19 can then be removed from the section 13 for further processing by an aspiration capillary 22, which is indicated diagrammatically and may, for example, be disposed on a movable holder.

The angle, at which the needle is disposed with respect to the tissue, is relatively immaterial. An angle of about 45 to 60° has proven to be advantageous. However, other angles also bring about the desired result and, at most, only result in a somewhat longer processing time.

As stated above, the exact positioning of the oscillating tip 17 of the needle can be effected automatically with the holder 21 with the help of a sensor. This sensor may, for example, be coupled with an oscillating drive mechanism 20 or also positioned on the support 11.

The FIGURE shows the apparatus for effecting the above-mentioned first method according to the invention, for which the tissue region 19 is detached in one piece from the tissue section 13 that is shown. For this method, the frequency of oscillations of the needle preferably is adjusted so that transverse oscillations do not occur. Only in this way can a narrow cut be guided through the tissue along the line 14 forming the boundary of the tissue region 19.

It is, of course, also conceivable to provide a different construction the inventive apparatus with a needle, which is driven to oscillate transversely, or to adjust the frequency of the device, shown in the FIGURE, so that transverse resonance oscillations also occur in the tip region of the needle in addition to the primary longitudinal oscillations generated. This second mode of operation is particularly suitable for dissecting tissue sections, which contain several small suspicious tissue regions. These tissue regions can conveniently be severed piece by piece from the section with the transversely oscillating tip, the pieces collecting in the liquid 15, with which they can be aspirated easily with the capillary 22 and collected.

With both methods, the apparatus, with which a micro-dissection can be carried out easily and inexpensively, is made available pursuant to the invention.

Though the present invention was shown and described with references to the preferred embodiments, such are merely illustrative of the present invention and are not to be construed as limitation thereof and various modifications of the present invention will be apparent to those skilled in the art. It is therefore not intended that the present invention be limited to the disclosed embodiments or details thereof, and the present invention includes all variations and/or alternative embodiments within the spirit and scope of the present invention as defined by the appended claims.

What is claimed is:

1. An apparatus for micro-dissection of a flat section of tissue secured to a support, the apparatus comprising a fine needle (18) having a tip for severing the tissue; means for moving the needle (18) along three axes for proper positioning the tip (17) of the needle (18) relative to the tissue; and an oscillating drive mechanism (20) for oscillating the needle at least in one of longitudinal and transverse directions at a predetermined amplitude and frequency.

2. The apparatus of claim 1, wherein the frequency is in the ultrasonic range.

3. The apparatus of claim 1, wherein the oscillating drive mechanism and the needle are coupled for producing a longitudinal oscillation, the operational frequency being selected so that, in addition to the longitudinal oscillations, transverse resonance oscillations can also occur in the region of the tip (17) of the needle (18).

4. The apparatus of claim 1, wherein the needle is formed of steel.

5. The apparatus of claim 1, wherein the oscillating drive mechanism is a piezo element.

6. The apparatus of claim 1, further comprising a sensor for determining an optimum position of the tip (17) of the needle during the operating of the apparatus.

7. The apparatus of claim 1, wherein the moving means comprises a holder (21); and the oscillating drive mechanism (20) is supported on the holder (21) and connects the needle (18) with the holder.

8. The apparatus of claim 1, further comprising optical means for controlling displacement of the needle tip.

* * * * *